(12) United States Patent
Bartsch et al.

(10) Patent No.: US 10,262,907 B1
(45) Date of Patent: Apr. 16, 2019

(54) DYE AND PRY PROCESS FOR REMOVING QUAD FLAT NO-LEAD PACKAGES AND BOTTOM TERMINATION COMPONENTS

(71) Applicant: International Business Machines Corporation, Armonk, NY (US)

(72) Inventors: Tim A. Bartsch, Stewartville, MN (US); Jennifer Bennett, Rochester, MN (US); James D. Bielick, Pine Island, MN (US); David J. Braun, St. Charles, MN (US); John R. Dangler, Rochester, MN (US); Stephen M. Hugo, Stewartville, MN (US); Theron L. Lewis, Rochester, MN (US); Timothy P. Younger, Rochester, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/818,953

(22) Filed: Nov. 21, 2017

(51) Int. Cl.
*B23K 31/02* (2006.01)
*H01L 21/02* (2006.01)
*H05K 3/34* (2006.01)
*H01L 21/60* (2006.01)
*H01L 21/66* (2006.01)
(Continued)

(52) U.S. Cl.
CPC ......... *H01L 22/12* (2013.01); *G01N 21/9505* (2013.01); *H01L 21/4842* (2013.01); *H01L 24/98* (2013.01); *H01L 23/49503* (2013.01); *H01L 2924/20103* (2013.01); *H01L 2924/20104* (2013.01); *H01L 2924/3512* (2013.01)

(58) Field of Classification Search
None
See application file for complete search history.

(56) References Cited

U.S. PATENT DOCUMENTS 5,651,493 A * 7/1997 Bielick ............... B23K 31/02
228/105
6,342,400 B1 * 1/2002 DePetrillo ............ G01N 19/08
228/105
(Continued)

OTHER PUBLICATIONS

Cascade Engineering Services, Inc., "Dye and Pry of BGA Solder Joints," Downloaded from the Internet, Jun. 28, 2017, www.cascade-eng.com/docs/CS_FA_01.pdf, 5 pages.
(Continued)

*Primary Examiner* — Khaja Ahmad
(74) *Attorney, Agent, or Firm* — Cantor Colburn LLP; Tihon Poltavets

(57) ABSTRACT

Embodiments of the invention include a dye and pry process for removing quad flat no-lead (QFN) packages and bottom termination components (BTC) from card assemblies. Aspects of the invention include immersing a semiconductor package assembly in a solution comprising dye and placing the immersed semiconductor package assembly under vacuum pressure. Vacuum conditions ensure that the dye solution is pulled into any cracks in the solder formed between the semiconductor package assembly and the QFN package or BTC. The package assembly is dried and a hole is drilled to expose a bottom surface of the QFN package or BTC. The QFN package or BTC is then removed by applying a force to the exposed bottom surface. The semiconductor package assembly can then be inspected for the dye to locate cracks.

13 Claims, 7 Drawing Sheets

(51) Int. Cl.
*G01R 31/02* (2006.01)
*H05K 1/02* (2006.01)
*G01R 31/04* (2006.01)
*H01L 23/00* (2006.01)
*H01L 21/48* (2006.01)
*G01N 21/95* (2006.01)
*H01L 23/495* (2006.01)

(56) References Cited

U.S. PATENT DOCUMENTS

| | | |
|---|---|---|
| 7,444,012 B2 | 10/2008 | White et al. |
| 7,845,849 B1 | 12/2010 | Choi et al. |
| 7,991,214 B1 | 8/2011 | Choi et al. |
| 8,638,564 B2 | 1/2014 | Buschel et al. |
| 9,137,898 B2 | 9/2015 | Frasco |
| 2013/0070434 A1* | 3/2013 | Buschel .......... H05K 3/00 361/757 |

OTHER PUBLICATIONS

Lin et al., "Package characterization on advanced NBA-QFN structure," 5th International Microsystems Packaging Assembly and Circuits Technology Conference, IMPACT, 2010, 4 pages.
Tsai et al., "Development of a Pre-mold Lead-frame for multi-row QFN package," 6th International Microsystems, Packaging, Assembly and Circuits Technology Conference, IMPACT, 2011, 3 pages.

* cited by examiner

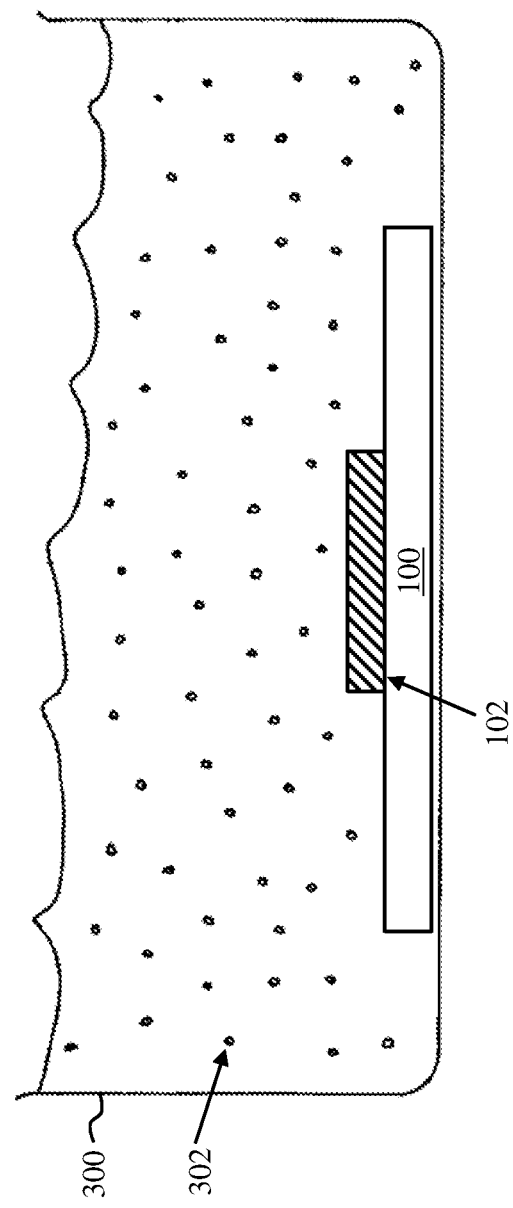

DYE AND PRY PROCESS FOR REMOVING QUAD FLAT NO-LEAD PACKAGES AND BOTTOM TERMINATION COMPONENTS

BACKGROUND

The present invention generally relates to equipment for testing semiconductor devices, and more specifically, to a dye and pry process for removing quad flat no-lead (QFN) packages and bottom termination components (BTC) from card assemblies.

Most integrated circuit components that are attached to a printed circuit board (PCB) are attached using mechanical means, such as soldering. In the past, when devices were relatively simple and included only a few leads going from each component to the board, a visual inspection could be made to determine whether the component-to-board bonding had been adequate and whether a good mechanical connection had been obtained with proper solder flow. Conventional surface mount technologies (SMT), however, are far more complicated and densely packed than legacy packages. For example, Land Grid Array (LGA) wiring/pad designs for silicon chip interconnection and Ball Grid Array (BGA) and Column Grid Array (CGA) type modules for silicon chip attachment or first level package attachment to a second level board electronic packaging assembly offer increased wire density over older peripheral component attachment schemes. Unfortunately, solder joints that are made on these more complicated packages cannot be visually inspected beneath the chip or component bodies after carrier attachment.

Instead, conventional packages are typically assessed using a destructive dye and pry technique. The "dye and pry" technique relies on a liquid dye that penetrates into existing micro cracks or under open solder balls to reveal defects on the solder ball to pad interface. This technique is a destructive test that requires the tested package to be submerged in dye and then baked at a relatively high temperature until the dye has set.

SUMMARY

Embodiments of the present invention are directed to a method for inspecting solder joints of a semiconductor package assembly having a quad flat no-lead (QFN) package or bottom termination component (BTC). A non-limiting example of the method includes immersing the semiconductor assembly in a solution including a dye and placing the immersed semiconductor package assembly under vacuum pressure. Vacuum conditions ensure that the dye solution is pulled into any cracks in the solder formed between the semiconductor package assembly and the QFN package or BTC. The package assembly is dried and a hole is drilled to expose a bottom surface of the QFN package or BTC. The QFN package or BTC is then removed by applying a force to the exposed bottom surface. The semiconductor package assembly can then be inspected for the dye to locate cracks.

Embodiments of the present invention are directed to a method for removing a component from a printed circuit board (PCB). A non-limiting example of the method includes drilling a hole through a portion of the PCB and a die paddle of the component to expose a bottom surface of the component. A punch tool is inserted into the hole to contact the exposed bottom surface of the component and a force is applied to the punch tool to remove the component from the PCB.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 3 depicts a cross-sectional view of a PCB and QFN package submerged in dye according to one or more embodiments of the invention;

Figure 1:
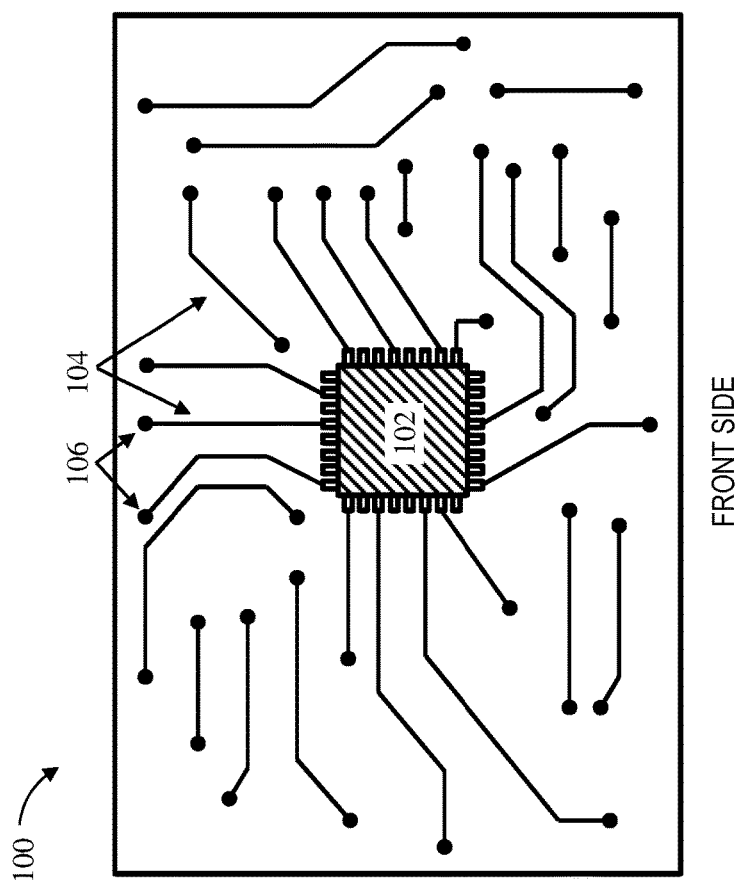
FIG. 1 depicts a front side view of a printed circuit board (PCB) according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

The present invention is directed towards equipment and methods for testing, validating, and monitoring semiconductor devices. Accordingly, the present invention will now be described with reference to the drawings, wherein like reference numerals are used to refer to like elements throughout. It should be understood that the description of these aspects are merely illustrative and that they should not be taken in a limiting sense. In the following description, for purposes of explanation, numerous specific details are set forth in order to provide a thorough understanding of the present invention. It will be evident to one skilled in the art, however, that the present invention may be practiced without these specific details.

For the sake of brevity, conventional techniques related to a semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the present invention, as previously noted herein, the dye and pry technique is a test method for testing semiconductor packages. Dye and pry is a destructive test that includes submerging a package or device to be tested in dye and baking the package at a relatively high temperature until the dye has set. After letting the dye dry, the package is pried off its printed circuit board (PCB) and the solder balls are inspected for the presence of the dye. Solder joints with pre-existing cracks are marked by the dried, typically red dye. In this manner, the dye reveals any inter-facial connection problem areas. Examples of defects that can be identified with the use of this method include solder opens, solder insufficiency, secondary solder cracking from partial reflow during subsequent assembly or local rework adjacent to the package, solder dewets, contamination, voids, pad delamination from excessive heat application during solder rework, and liquid solder joint separation due to card warpage during rework. In addition, this analysis method is also used on assemblies after Accelerated Thermal Cycling (ATC) reliability tests or power cycling to assess the robustness of package interconnections against fatigue related failures on card interfaces, module interfaces, intermetallic compound interfaces, and inter-granular solder cracking intrinsic to solder balls, solder columns, and C4 solder bumps.

While well-suited to land grid array (LGA), ball grid array (BGA) and column grid array (CGA) wiring/pad designs, there are challenges in adopting the dye and pry technique to more advanced SMT platforms. For example, dye and pry are somewhat limited and error prone when applied to Quad flat no-lead (QFN) packages or bottomside terminated components (BTC). QFN (also known as lead frame-style) is a surface-mount technology that connects ICs to a surface of a PCB without through-holes. Flat no-lead packages are typically near chip scale plastic encapsulated packages made with a planar copper lead frame substrate. Perimeter lands (contacts) on the package bottomside provide electrical connections to the PCB.

There are two conventional approaches to dye and pry characterization analysis for QFN packages and BTC type components. In one option, the component is sheared off a semiconductor package assembly (e.g., a PCB) with a flat bladed tool. Alternatively, a metal block can be glued or otherwise affixed to the top of the component and a pulling force can be applied (using, e.g., a pull tester) to the metal block to rip the component from the board. Either technique carries a relatively high risk of component and solder joint damage. Moreover, it is virtually impossible to get a pry tool between the component and the PCB due to the low profile of a BTC component or QFN package.

Most attempts result in the component breaking into smaller pieces and the solder joints being damaged (sheared or smeared). Solder damage is especially problematic with BTCs having large centered thermal pads soldered to the PCB. Consequently, a thorough analysis of QFN packages and BTC components is difficult if not impossible and the value of the otherwise straightforward dye and pry technique is greatly diminished.

Turning now to an overview of aspects of the present invention, one or more embodiments of the invention provide an improved dye and pry process for removing QFN packages and BTC components from card assemblies. The method includes drilling a hole or multiple holes through the backside of the package after the dye and bake to expose a bottom surface of the QFN package or BTC component. Each hole is located and sized to be as small as possible based on the thickness of the component and the size of any center soldered termination/thermal pad. While a single hole is sufficient for most applications, in some situations, e.g., packages having multiple soldered terminations/thermal pads between the component and assembly, multiple holes can be drilled. Once drilled, a tool is inserted into the hole(s) and subjected to a sudden or controlled load to remove the component from the package without causing the solder joint damage associated with conventional pry-based techniques. The controlled load can be a machine with a load cell that can monitor forces and provide data to be used for analytical work. The package can then be inspected for defects. Advantageously, this technique ensures that the sample component or device keeps the monolithic shape and keeps any preexisting attributes (i.e., solder joint structure) whole for analysis.

Turning now to a more detailed description of aspects of the present invention, FIG. 1 depicts a front side view of a PCB 100 according to one or more embodiments of the invention. In some embodiments of the present invention, the PCB 100 includes a QFN package or BTC component. For example, the PCB 100 can include a QFN package 102. In some embodiments of the present invention, the PCB 100 includes a plurality of electrical traces 104 coupled to one or more vias 106 for electrically coupling various board components (not depicted).

Figure 2A:
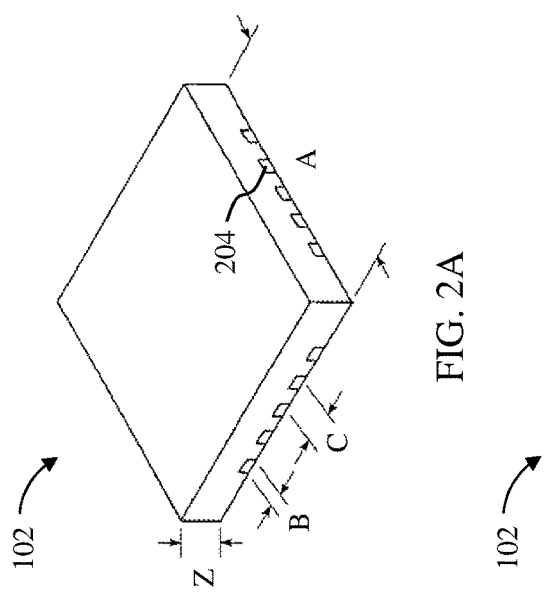
FIGS. 2A and 2B depict an isometric view and a bottom side view of a QFN package according to one or more embodiments of the invention.
Figure 2B:
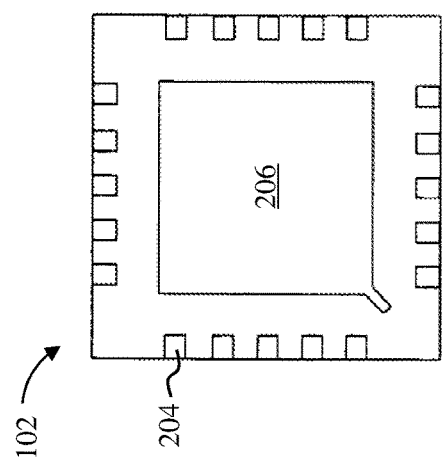

FIGS. 2A and 2B depict an isometric view and a bottom side view of the QFN package 102 (also known as a QFN chip) according to one or more embodiments of the invention. The QFN package 102 can range in a lateral dimension "A" from about 0.5 to 12.0 mm in increments of about 0.1 mm. In some embodiments of the present invention, the QFN package 102 includes one or more perimeter terminals 204 (also known as leads). Typical terminals range in width "B" from 0.15 to 0.5 mm and range in pitch "C" from 0.2 to 2.00 mm, although other dimensions are within the contemplated scope of the invention. In some embodiments of the present invention, the QFN package 102 includes an overall height "Z" of 0.1 to 5.0 mm. In some embodiments of the present invention, the QFN package 102 includes a die paddle 206 (also known as a conductive pad or thermal pad).

As depicted, the QFN package 102 includes 5 leads per side for a total of 20 leads. It is understood, however, that any number of leads can be provided. For example, the QFN package 102 can include 8, 12, or 20 leads per side. To form a second level interconnect, the QFN package 102 is mounted on a PCB (as depicted in FIG. 1). The mounting process involves soldering one or more of the perimeter terminals 204 and the die paddle 206 to pads on the PCB.

FIG. 3 depicts a cross-sectional view of the PCB 100 and QFN package 102 according to one or more embodiments of the invention. As depicted in FIG. 3, the PCB 100 and QFN package 102 are placed in a container 300, such as a beaker or a petri dish, and immersed in a solution of dye 302. Prior to immersion, the PCB 100 can be cut to any required sample size. The maximum sample size can be limited by equipment (e.g., dye pan size). The PCB 100 can be cut using any suitable technique known for cutting circuit boards without causing excessive vibrations on solder joints. For example, the PCB 100 can be cut using a diamond saw.

In some embodiments of the present invention, the PCB 100 is pre-cleaned prior to immersion. The flux can be removed using any suitable process. The pre-clean process can include, for example, a polar solvent or a solution of water and saponifier and ensures that any flux residue on the PCB 100 (resulting from, e.g., a no clean soldering process) is removed prior to immersion. Flux can cause false calls and can prevent dye ingress into cracks. In some embodiments of the present invention, the PCB 100 is pre-cleaned using a cleaning mixture of 75% isopropyl alcohol and 25% water. To help remove the flux, the cleaning mixture can be heated and agitated. In some embodiments of the present invention, the cleaning mixture is heated to a temperature of between 50 and 70 degrees Celsius. In some embodiments of the present invention, the PCB 100 is soaked in the cleaning mixture for several hours (e.g., 2-3 hours or longer).

After pre-cleaning, the PCB 100 and QFN package 102 are immersed in the solution of dye 302. The dye 302 can be any dye suitable for dye and pry processing, such as, for example, red tracer dye. In some embodiments of the present invention, the dye 302 material is selected such that the dye 302 can be easily photographed with white light. As depicted, the PCB 100 and QFN package 102 are fully immersed in the dye 302. Alternatively, the PCB 100 and QFN package 102 can be partially immersed while only the portion of interest is wholly immersed.

In some embodiments of the present invention, the submerged PCB 100 and QFN package 102 are put in a conventional vacuum chamber oven. Vacuum conditions allow for the dye 302 to be pulled into any cracks that exist in the solder or bonding pads. In some embodiments of the present invention, the PCB 100 and QFN package 102 are placed under a vacuum of about 27 inches of mercury for about 10 minutes, although other vacuum pressures and durations are within the contemplated scope of the invention. In some embodiments of the present invention, the PCB 100 and QFN package 102 are left under vacuum conditions for more than an hour, such as, for example, 4 or 8 hours.

After the PCB 100 and QFN package 102 are dyed, the PCB 100 is pulled from the container 300 and the excess dye 302 is blown off. The PCB 100 is then placed in an oven for baking. Baking ensures that the dye 302 that has penetrated cracks in the PCB 100 or QFN package 102 properly sets. The baking temperature is adjusted based on the sensitivity of the samples tested. In some embodiments of the present invention, the PCB 100 and QFN package 102 are baked at a temperature of about 85 to about 120 degrees Celsius, although other baking temperatures are within the contemplated scope of the invention. The total baking time varies depending on the sample to be tested. In some embodiments of the present invention, the PCB 100 and QFN package 102 are baked for a minimum of 8 hours. In some embodiments of the present invention, the PCB 100 and QFN package 102 are baked for at least 24 hours, although other baking times are within the contemplated scope of the invention. After baking, the PCB 100 and QFN package 102 are allowed to cool to room temperature.

Figure 4:
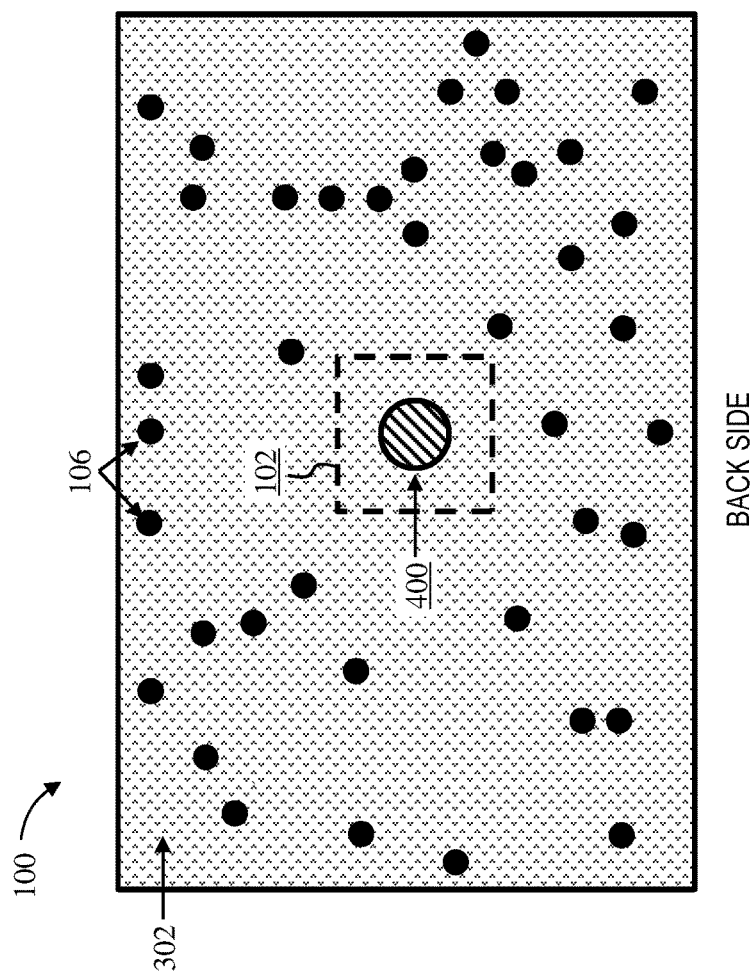
FIG. 4 depicts a back side view of the PCB and QFN package of FIG. 3 after baking the PCB according to one or more embodiments of the invention.

FIG. 4 depicts a back side view of the PCB 100 and QFN package 102 after baking according to one or more embodiments of the invention. As depicted in FIG. 4, the surface of the PCB 100 is covered in dye 302. As discussed previously herein, a hole 400 is drilled into the back side of the PCB 100 to expose a bottom surface of the QFN package 102. A tool, such as a punch drive, is inserted into the hole 400 against the bottom surface of the QFN package 102 to pop the QFN package 102 off the PCB 100. Before drilling, the hole 400 position and size is determined. The hole 400 is positioned and sized in part to sufficiently weaken the strength of the center thermal pad solder joint (i.e., solder applied to the die paddle 206 depicted in FIG. 2) under the QFN package 102. Weakening the center thermal pad solder joint allows for an improved separation of the QFN package 102 from the PCB 100. In some embodiments of the present invention, a drill bit is selected such that the diameter of the hole 400 will remove 10, 15, 20, 25, 40, 50, 75, 80, 90, 95 percent of the die paddle 206. In some embodiments of the present invention, the size of the hole 400 is made to be as small as possible (i.e., to minimally accommodate the smallest punch tool that is sufficient to remove the QFN package 102). In some embodiments of the present invention, the size of the hole 400 is less than the diameter of the die paddle 206. In some embodiments of the present invention, multiple holes are drilled into the back side of the PCB 100. As discussed previously herein, multiple holes can be used in cases where a single hole is not sufficient to weaken the connection between the QFN package 102 and the PCB 100. For example, multiple holes are useful in applications having multiple soldered terminations/thermal pads, a single oversized thermal pad, or irregularly shaped thermal pad(s) between the component and assembly.

Because of the relatively small hole sizes in typical applications, the hole 400 is drilled using any suitable high RPM precision drilling machine. For example, the drilling machine can operate at 1000 to 3000 rpms. In some embodiments of the present invention, the size of the drill bit is adjusted based on the thickness of the PCB 100. In some embodiments of the present invention, the thickness is measured using a micrometer.

Once the hole 400 is drilled, a tool, such as a punch drive, is inserted into the hole 400 against the bottom surface of the QFN package 102. A sudden or controlled load is applied to the tool to remove the QFN package 102 from the PCB 100. In some embodiments of the present invention, the load is applied using a machine with a load cell. In this manner, the force applied to the QFN package 102 can be monitored to provide analytical data. Advantageously, removing the QFN package 102 in this manner preserves the monolithic shape of the QFN package 102 and solder joint structure for analysis. In applications requiring two or more holes, the punch tool can include a corresponding number of extending members (flanges, fingers, tines, etc.) such that a force can be simultaneously applied to the component through each hole.

Figure 5:
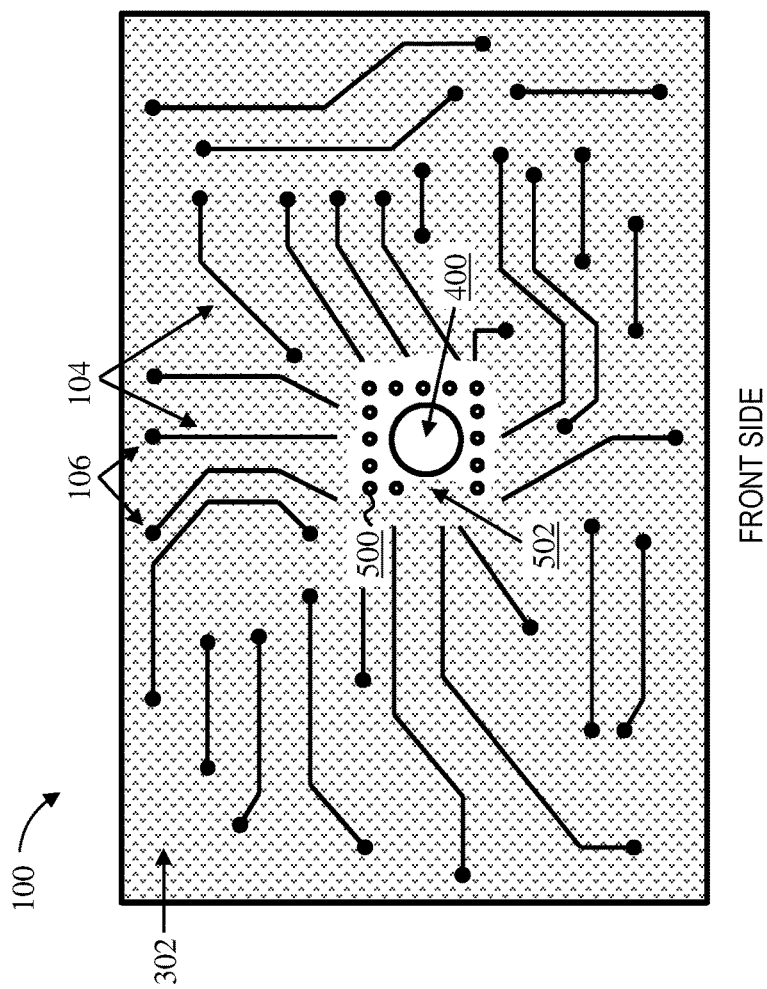
FIG. 5 depicts a front side view of the PCB of FIG. 4 after removing the QFN package according to one or more embodiments of the invention.

FIG. 5 depicts a front side view of the PCB 100 after removing the QFN package 102 according to one or more embodiments of the invention. The PCB 100 can now be analyzed for signs of die ingress into, e.g., damaged solder joints. The surface of the PCB 100 that was under the QFN package 102 is now exposed and reveals a plurality of bottomside contacts 500. These bottomside contacts 500 provided electrical contact to the QFN package 102. As depicted in FIG. 5, the dye 302 has covered a surface 502 of one or more bottomside contacts 500, indicating dye ingress into cracks in some of the solder joints between the QFN package 102 and the PCB 100.

Figure 6:
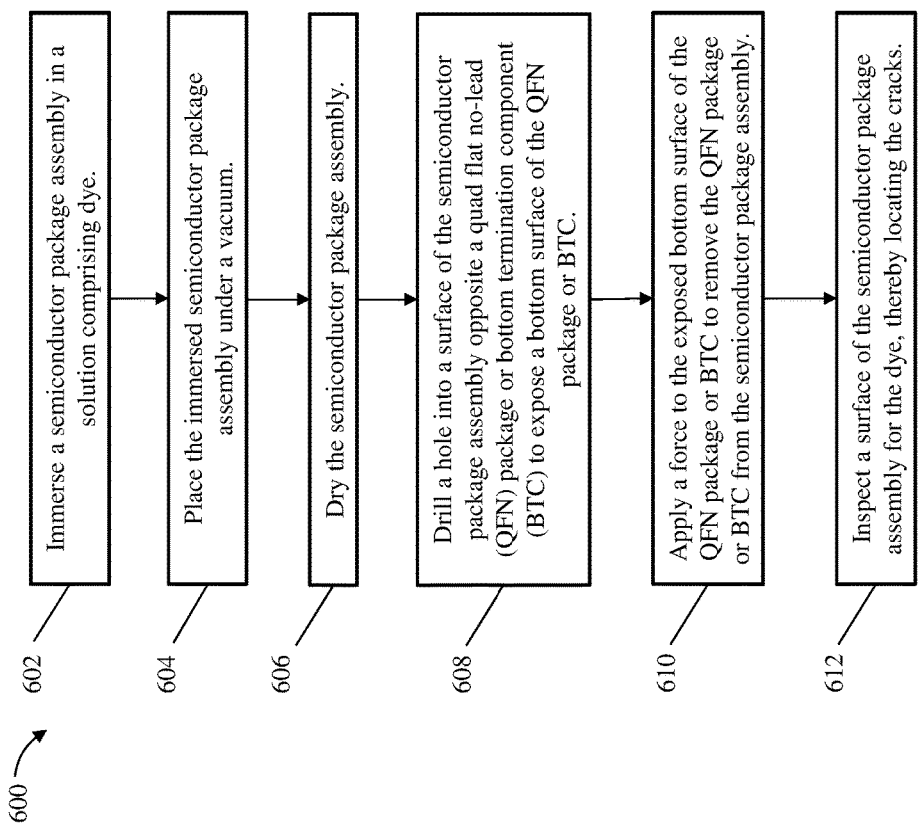
FIG. 6 depicts a flow diagram of a method for inspecting solder joints of a semiconductor package assembly having a QFN package or BTC component according to one or more embodiments of the invention.

FIG. 6 depicts a flow diagram of a method for inspecting solder joints of a semiconductor package assembly having a QFN package or BTC component according to one or more embodiments of the invention. The method 600 includes immersing, at block 602, the semiconductor package assembly in a solution including dye.

The method 600, at block 604, includes placing the immersed semiconductor package assembly under a vacuum. Vacuum conditions ensure that the dye solution will be pulled into any cracks that exist in solder formed between the semiconductor package assembly and the QFN package or BTC.

At block 606, the semiconductor package assembly is dried. As discussed previously herein, the semiconductor package assembly is dried by baking the assembly until the dye sets. The baking temperature is adjusted based on the sensitivity of the samples tested. In some embodiments of the present invention, baking occurs at a temperature of about 85 to about 120 degrees Celsius. The total baking time varies depending on the sample to be tested and can range from a few minutes to over 24 hours.

As discussed previously herein, a hole is drilled at step 608 into a surface of the semiconductor package assembly opposite the QFN package or BTC to expose a bottom surface of the QFN package or BTC. The hole is large enough to allow for a punch tool to be inserted into the hole and against the exposed bottom surface of the QFN package or BTC.

At step 610 a force is applied to the exposed bottom surface of the QFN package or BTC to remove the component from the semiconductor package assembly. In some embodiments of the present invention, a punch tool is inserted against the exposed bottom surface of the QFN package or BTC and tapped until the component is removed.

Once the component is removed, the surface of the semiconductor package assembly is inspected at step 612 for the dye to indicate the presence of solder cracks. The package assembly can be visually or mechanically inspected using any suitable process. In some embodiments of the present invention, the package assembly is inspected using an optical microscope at a power of about 150×, although other optical powers are within the contemplated scope of the invention.

Figure 7:
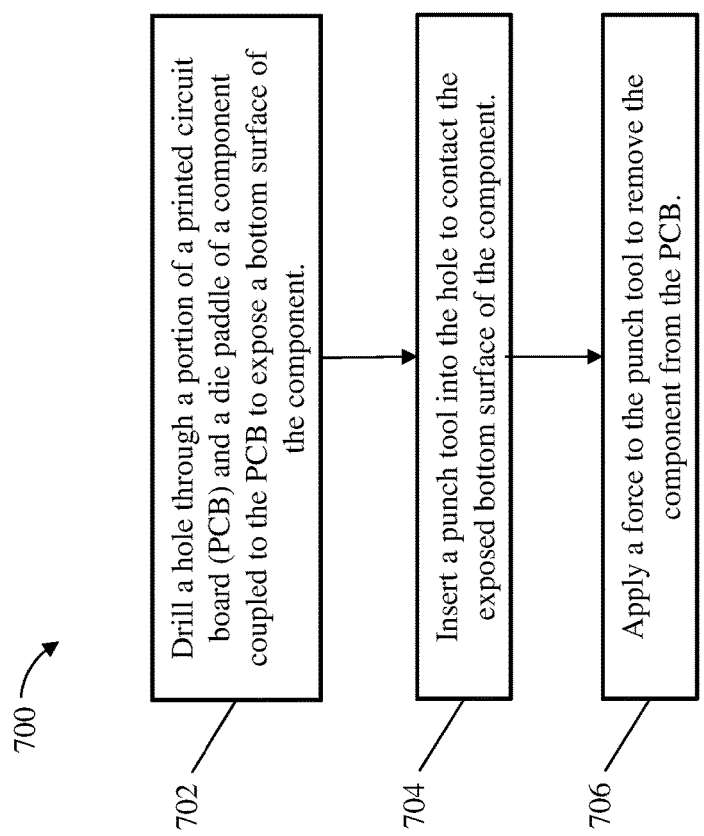
FIG. 7 depicts a flow diagram of a method for removing a component from a PCB according to one or more embodiments of the invention.

FIG. 7 depicts a flow diagram of a method for removing a component from a PCB according to one or more embodiments of the invention. The method 700 includes, at step 702, drilling a hole through a portion of the PCB and a die paddle of a component coupled to the PCB to expose a bottom surface of the component. At step 704, the method includes inserting a punch tool into the hole to contact the exposed bottom surface of the component. A force is applied to the punch tool, at step 706, to remove the component from the PCB.

Additional processes may also be included. It should be understood that the processes depicted in FIGS. 6 and 7 represent illustrations and that other processes may be added or existing processes may be removed, modified, or rearranged without departing from the scope and spirit of the present disclosure.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Similarly, the term "coupled" and variations thereof describes having a communications path between two elements and does not imply a direct connection between the elements with no intervening elements/connections between them. All of these variations are considered a part of the specification. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of inspecting solder joints of a semiconductor package assembly having a quad flat no-lead (QFN) package or bottom termination component (BTC), the method comprising:
    immersing the semiconductor package assembly in a solution comprising dye;
    placing the immersed semiconductor package assembly under a vacuum such that, when cracks exist in solder formed between the semiconductor package assembly and the QFN package or BTC, the dye solution is pulled into the cracks;
    drying the semiconductor package assembly;
    drilling a hole into a surface of the semiconductor package assembly opposite the QFN package or BTC to expose a bottom surface of the QFN package or BTC;
    applying a force to the exposed bottom surface of the QFN package or BTC to remove the QFN package or BTC from the semiconductor package assembly; and
    inspecting a surface of the semiconductor package assembly for the dye, thereby locating the cracks.

2. The method of claim 1, wherein removing the QFN package or BTC from the semiconductor package assembly exposes one or more bottomside contacts.

3. The method of claim 1, wherein inspecting a surface of the semiconductor package assembly for the dye comprises inspecting a surface of one or more exposed bottomside contacts.

4. The method of claim 1, wherein the dye solution comprises red tracer dye.

5. The method of claim 1, wherein the vacuum comprises a vacuum pressure of about 27 inches of mercury (Hg).

6. The method of claim 1 further comprising leaving the semiconductor package assembly under vacuum for at least 10 minutes.

7. The method of claim 1, wherein drying the semiconductor package assembly comprises baking the semiconductor package assembly at a temperature between 85 to 120 degrees Celsius.

8. The method of claim 7 further comprising baking the semiconductor package assembly for at least 8 hours.

9. The method of claim 1, wherein drilling a hole into a surface of the semiconductor package assembly comprises selecting a drill bit that comprises a smaller diameter than a diameter of a die paddle of the QFN package or BTC.

10. The method of claim 9, wherein drilling a hole into a surface of the semiconductor package assembly further comprises removing a portion of the die paddle.

11. The method of claim 1, wherein applying a force to the exposed bottom surface of the QFN package or BTC comprises inserting a punch tool into the hole in the semiconductor package assembly.

12. The method of claim 1, wherein applying a force to the exposed bottom surface of the QFN package or BTC comprises using a machine with a load cell such that the applied force can be monitored to provide analytical data.

13. The method of claim 1 further comprising inspecting the surface of the semiconductor package assembly with an optical microscope.

* * * * *